(12) United States Patent
King

(10) Patent No.: US 6,918,898 B2
(45) Date of Patent: Jul. 19, 2005

(54) CLOSED DRAINAGE SYSTEM FOR IRRIGATING OSTOMIES

(76) Inventor: Lori L. King, 148 Sutherlin Ave., Danville, VA (US) 24541

( * ) Notice: Subject to any disclaimer, the term of this patent is extended or adjusted under 35 U.S.C. 154(b) by 384 days.

(21) Appl. No.: 10/166,368

(22) Filed: Jun. 11, 2002

(65) Prior Publication Data

US 2003/0229324 A1 Dec. 11, 2003

(51) Int. Cl.[7] .................................................. A61F 5/44
(52) U.S. Cl. ....................................... 604/334; 604/277
(58) Field of Search .................... 604/277, 332–345, 604/355, 356, 540; 4/144.1, 144.2, 144.3, 144.4; 206/438

(56) References Cited

U.S. PATENT DOCUMENTS

| | | | |
|---|---|---|---|
| 2,154,202 A | | 4/1939 | Gricks |
| 2,223,566 A | | 12/1940 | Koch |
| 2,331,226 A | * | 10/1943 | Pritchard ..................... 604/334 |
| 2,689,567 A | * | 9/1954 | Welch ........................ 604/277 |
| 2,869,547 A | * | 1/1959 | Yohe .......................... 604/334 |
| 3,055,365 A | | 9/1962 | Tezak |
| 3,672,370 A | * | 6/1972 | Marsan ....................... 604/277 |
| 3,830,235 A | | 8/1974 | Marsan |
| 4,134,404 A | | 1/1979 | Williams, Jr. |
| 4,586,927 A | * | 5/1986 | Jensen ........................ 604/342 |
| 4,766,622 A | * | 8/1988 | Pacelli .......................... 4/661 |
| 4,769,015 A | * | 9/1988 | Bloxom, Jr. ................ 604/277 |
| 4,804,373 A | * | 2/1989 | Bloxom, Jr. ................ 604/277 |
| 5,236,426 A | * | 8/1993 | Schottes et al. ............ 604/334 |
| 5,330,447 A | * | 7/1994 | Barth ......................... 604/277 |
| 5,470,325 A | * | 11/1995 | Fundock ..................... 604/332 |
| 5,503,633 A | * | 4/1996 | Saunders et al. ........... 604/332 |
| 5,738,661 A | * | 4/1998 | Larice ........................ 604/180 |
| 5,738,668 A | * | 4/1998 | Bugajski .................... 604/332 |
| 5,951,532 A | | 9/1999 | Olsen |
| 6,532,971 B2 | * | 3/2003 | Deecki .................... 134/22.18 |
| 6,695,825 B2 | * | 2/2004 | Castles ....................... 604/332 |

* cited by examiner

*Primary Examiner*—Larry I. Schwartz
*Assistant Examiner*—Michael G. Bogart
(74) *Attorney, Agent, or Firm*—Richard C. Litman

(57) ABSTRACT

A closed drainage system for irrigating ostomies which consists of 1) a standard hospital enema bag and tube, 2) a colostomy bag with a stop cock valve and with a flapped opening for receiving an enema bag tube, 3) a collection bag tube, and 4) a collection bag with hanging hooks and a drain spout. The system allows for large volume ostomy irrigation and, further, allows for the products of irrigation to be enclosed until their controlled removal thereby containing offensive odors, preventing soiled sheets and reducing the risk of spreading infectious diseases.

9 Claims, 6 Drawing Sheets

CLOSED DRAINAGE SYSTEM FOR IRRIGATING OSTOMIES

BACKGROUND OF THE INVENTION

1. Field of the Invention

The present invention relates to medical devices for ostomy irrigation and, more particularly, to a closed drainage system which allows for the irrigation of an ostomy without requiring the user to stand over a toilet or subjecting the user, and others in his or her vicinity, to offensive odor, soiled sheets or unsightly drainage of human waste. Significantly, in a hospital or other health care facility setting, the invention decreases the likelihood of spreading infectious disease—such as HIV, MRSA, VRE, and hepatitis—by minimizing or eliminating contact with human waste related to ostomy irrigation.

2. Description of the Related Art

A colostomy is a surgical procedure in which the colon or a portion thereof is removed and the digestive track is attached to an opening created in the abdominal wall, thereby, allowing digestive waste to pass through the abdomen. Typically, the waste is then collected by an impervious bag that is secured over the opening. The opening which results from a colostomy is known as an ostomy or a stoma, and the impervious bag that collects the digestive waste is known as a colostomy bag.

An individual who has had a colostomy must typically remove and empty the colostomy bag several times a day, and must irrigate the ostomy at least every other day to maintain good health and sanitation. An ostomy is irrigated by applying flowing water into the ostomy, and then allowing the water to drain. The prior art discloses several devices for irrigating an ostomy in a sanitary manner in which the user must stand over or sit on a toilet. However, in a hospital or other health care facility setting, an individual with an ostomy may be confined to bed and therefore may be unable to position his or herself near a toilet. In such circumstance, flowing water is typically applied to the ostomy via a standard enema bag and enema bag tube. A basin or bed pan is typically placed under the individual to collect the water as it drains from the ostomy. Unfortunately though, irrigating an ostomy in this manner usually results in soiled sheets, unpleasant odors, unsightly and unsanitary drainage of human waste and, significantly, the increased chance of contact with human waste by a health care provider such as a nurse or nurse's aid. Furthermore, irrigation performed in this manner is often humiliating and embarrassing to the patient and/or the patient's guests or visitors.

Examples of ostomy irrigating devices in the prior art are provided by U.S. Pat. No. 2,154,202 to Gricks; U.S. Pat. No. 2,223,566 to Koch; U.S. Pat. No. 3,055,365 to Tezak; U.S. Pat. No. 3,830,235 to Marsan; and U.S. Pat. No. 4,134,404 to Williams, Jr. The devices taught by each of these patents allow for the application of flowing water to an ostomy via a receptacle that is secured to a user's waist. With each device, water continuously flows into, through, and out of the receptacle, irrigating the ostomy along the way. The flowing water exits the receptacle, in each device, via an opening or tube that is positioned over a toilet. Thus, the common drawback of all of these devices is that the user is required to stand over or sit on a toilet; therefore, these devices are not useful if the user is not in close proximity to a toilet.

Although not an ostomy irrigating device, the device taught by U.S. Pat. No. 5,951,532 to Olsen bears a faint structural resemblance to the lower section of the present invention. The Olsen patent teaches a colostomy bag to which an extension bag may be attached. The purpose of the extension bag is to allow for collection of a large amount of waste. However, the device does not have a means for receiving flowing water and therefore can not be used for irrigating an ostomy. Additionally, the bag extension is attached to the colostomy bag by means of a flange and coupling ring that do not, by themselves, allow for the cessation of waste flowing out of the colostomy bag when the bags are separated. Although a cap may be attached to the opening on the colostomy bag, the release of waste onto the user and offensive odor into the ambient air may occur between the time the extension bag is removed and the cap is attached.

Consequently, none of the above inventions and patents, taken either singly or in combination, is seen to describe the instant invention as claimed. Thus a closed drainage system for irrigating ostomies solving the aforementioned problems is desired.

SUMMARY OF THE INVENTION

The present invention is a closed drainage system for irrigating ostomies which consists of 1) a standard hospital enema bag and tube, 2) a colostomy bag with a stop cock valve and a flapped opening for receiving an enema bag tube, 3) a collection bag tube, and 4) a collection bag with hanging hooks and a drain spout. The system allows for large volume irrigation and, further, allows the products of the irrigation to be enclosed until their controlled removal.

Accordingly, it is a principal object of the invention to decrease the likelihood of spreading infectious disease—such as HIV, MRSA, VRE, and hepatitis—by minimizing or eliminating contact with human waste related to ostomy irrigation.

It is another object of the invention to eliminate the need for a person with an ostomy to stand over or sit on a toilet when irrigating the ostomy.

It is a further object of the invention to allow a patient confined to bed to irrigate an ostomy in a sanitary and dignified manner, i.e., in a manner that does not result in offensive odor, soiled sheets or unsightly mess.

Still another object of the invention is to provide a device for irrigating an ostomy that can attach to a standard colostomy bag flange, which is a flanged ring with adhesive backing that is typically secured to the abdomen of a person with an ostomy. The flange allows a colostomy bag to be easily attached and detached. The colostomy bag attaches to the flanged ring much like a tupperware lid attaches to a tupperware bowl, i.e., the colostomy bag and flange snap together to form an air-tight seal. Consequently, an irrigating system that uses the same flanged ring is also easily attached and detached and, further, does not necessitate the removal and replacement of the flanged ring for each irrigation.

Yet another object of the invention is to provide a device for irrigating ostomies that can also be used as a large volume colostomy bag for those occasions where a patient discharges large amounts of waste, such as when a patient has diarrhea.

Finally, it is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

DETAILED DESCRIPTION OF THE PREFERRED EMBODIMENT

Figure 1:
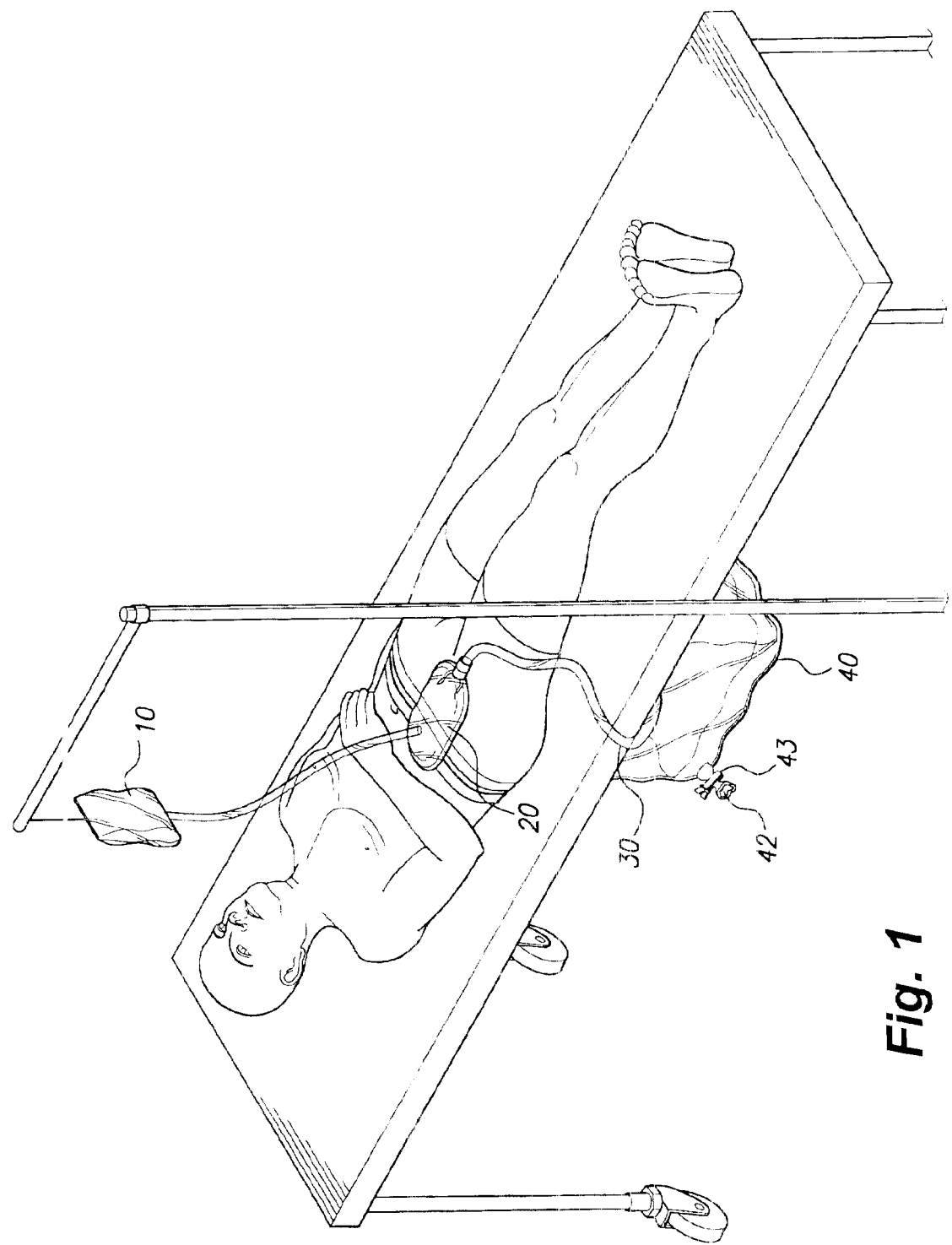
FIG. 1 is an environmental, perspective view of a closed drainage system for irrigating ostomies according to the present invention.

FIG. 1 of the drawings presents an environmental view of the closed drainage system for irrigating ostomies of the present invention. It will be appreciated from the view that the invention comprises four main components which are: a standard enema bag and tube 10, a colostomy bag 20, a collection bag 40, and a collection bag tube 30.

Figure 2:
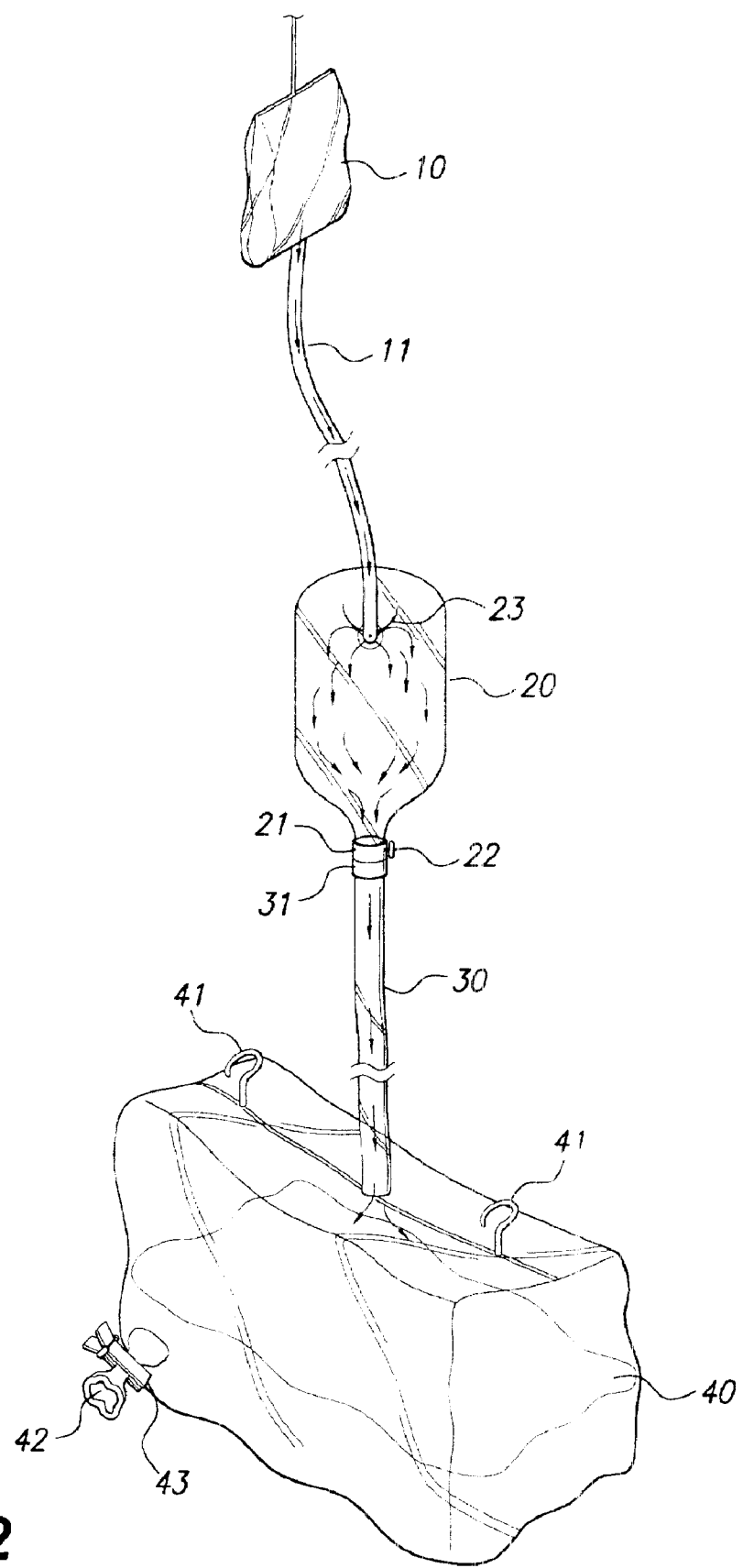
FIG. 2 is an elevational view of a closed drainage system for irrigating ostomies according to the present invention.

FIG. 2 of the drawings presents an elevation view of the preferred embodiment of the closed drainage system for irrigating ostomies and depicts a standard enema bag 10 suspended above a colostomy bag 20 that drains to a collection bag 40. The enema bag 10 is connected to the colostomy bag 20 by a standard enema bag tube 11 which allows water to flow from the enema bag 10 to the colostomy bag 20. One end of the enema bag tube 11 is attached to the base of the enema bag 10 and the other end is inserted into a flapped opening 23 on the colostomy bag 20.

The colostomy bag 20 has a front side and a back side. The flapped opening 23 is located on the front side and a rimmed opening (discussed below with reference to FIG. 4), that is shaped and dimensioned to be secured over an ostomy, is located on the back side. The colostomy bag 20 is preferably made of a transparent material for visualizing insertion of the enema tube into a patient's ostomy. Water flows from the enema bag tube into the user's ostomy and then drains into the colostomy bag via the rimmed opening. The products of ostomy irrigation, i.e., water and human digestive waste, flow out of the colostomy bag 20 via an opening at the base of the colostomy bag 20 that is fitted with a hard plastic fitting 21. The hard plastic fitting 21 mates to a similar fitting 31 that is attached to one end of the collection bag tube 30.

The collection bag tube 30 connects the colostomy bag 20 to the collection bag 40 and allows the products of ostomy irrigation to flow from the former to later. While the collection ba tube 30 and the collection bag 40 are shown to be made of a transparent material, they may also be constructed of an opague impervious material.

The collection bag 40 is dimensioned to accommodate large volumes of irrigation products and is equipped with two hanging hooks 41 that allow it to be hung from the rail or frame of a standard hospital bed or other bed. The collection bag tube 30 is attached to the top of the collection bag 40 thereby allowing irrigation products to flow freely into the collection bag 40. The collection bag is also equipped with a drain spout 42 that allows the bag to be easily drained by releasing a clamp 43 attached to the spout.

The hard plastic fittings 21 and 31, which connect the colostomy bag 20 to the collection bag tube 30, mate to form an air tight seal thereby allowing the products of irrigation to flow through the fittings without leakage. The fittings 21 and 31 can be separated to allow for drainage of the collection bag without interrupting an irrigation procedure. The colostomy bag fitting 21 contains stop cock valve 22 that interrupts the flow out of the colostomy bag before the fittings are separated.

Figure 3:
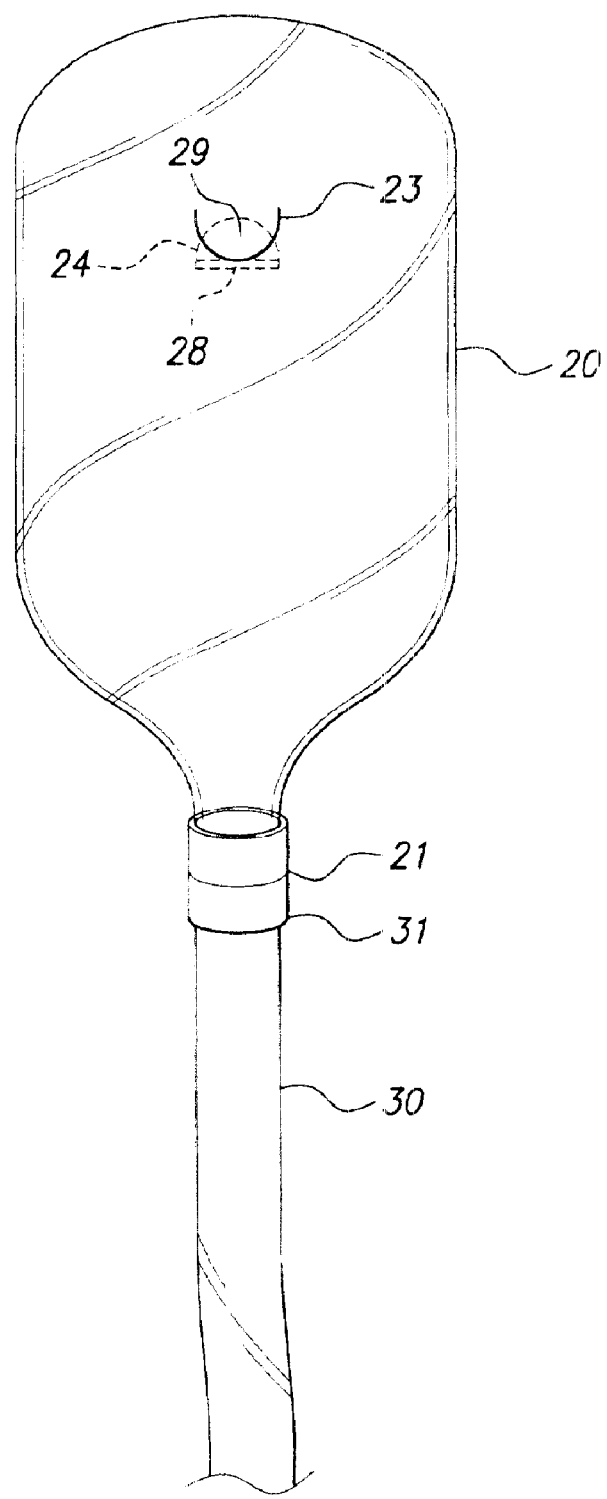
FIG. 3 is an elevational front view of the colostomy bag component according to the present invention.

FIG. 3 of the drawings presents a front view of the colostomy bag 20 and depicts the flapped opening 23 which consists of outer flap 29 and an inner flap 24. The outer flap 29 is semi-circular in shape and is formed by an opening in the surface of the colostomy bag 20. The inner flap 24, which is also semi-circular in shape, is attached to the inside of the colostomy bag 20 via an adhesive that is applied to a rectangular portion 28 of the inner flap.

Figure 4:
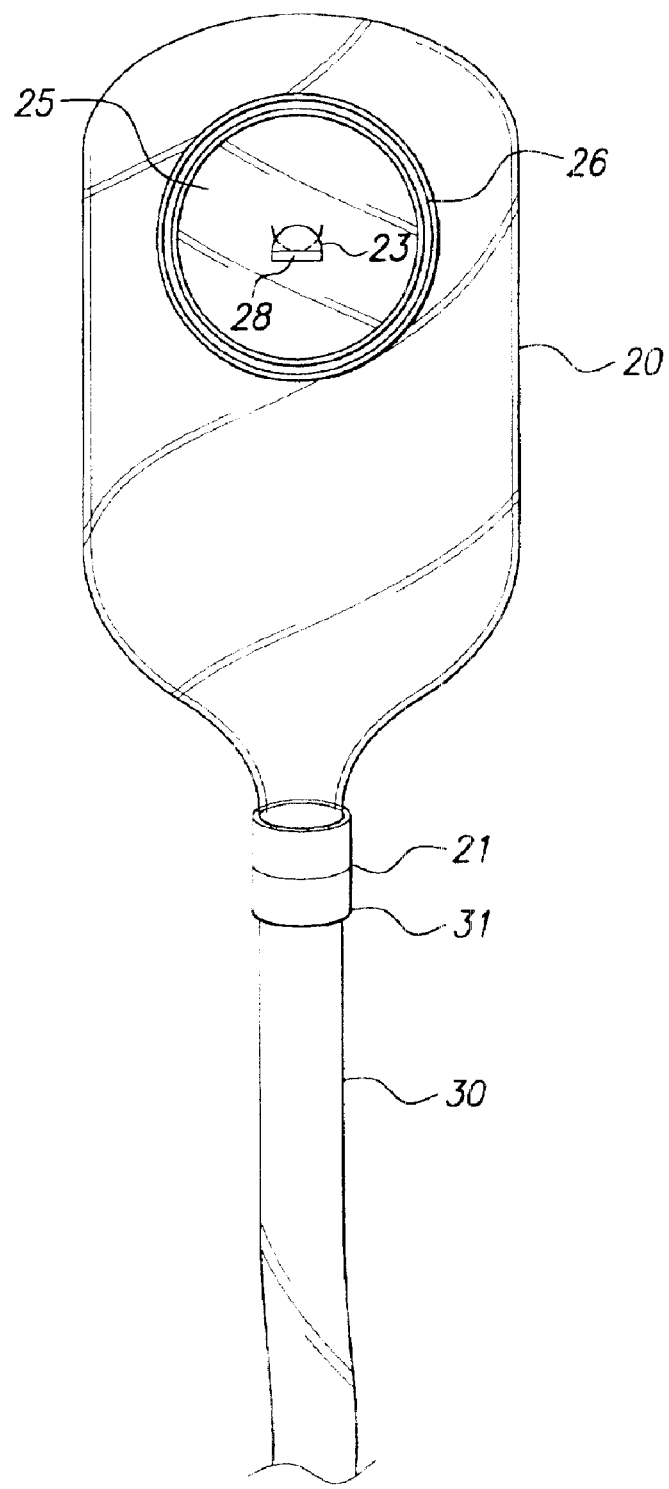
FIG. 4 is an elevational back view of the colostomy bag component according to the present invention.

FIG. 4 of the drawings presents a rear view of the colostomy bag 20 and depicts the rimmed opening 25 which is shaped and dimensioned to be secured over the user's ostomy via a standard ostomy flanged ring, which is a flanged ring with adhesive backing that is typically secured to the abdomen of a person with an ostomy. The flange allows a colostomy bag to be easily attached and detached. The rim 26 of the rimmed opening 25 attaches to the flange much like a tupperware lid to a tupperware bowl; hence, the rimmed opening and flange snap together to form an air-tight seal.

Figure 5:
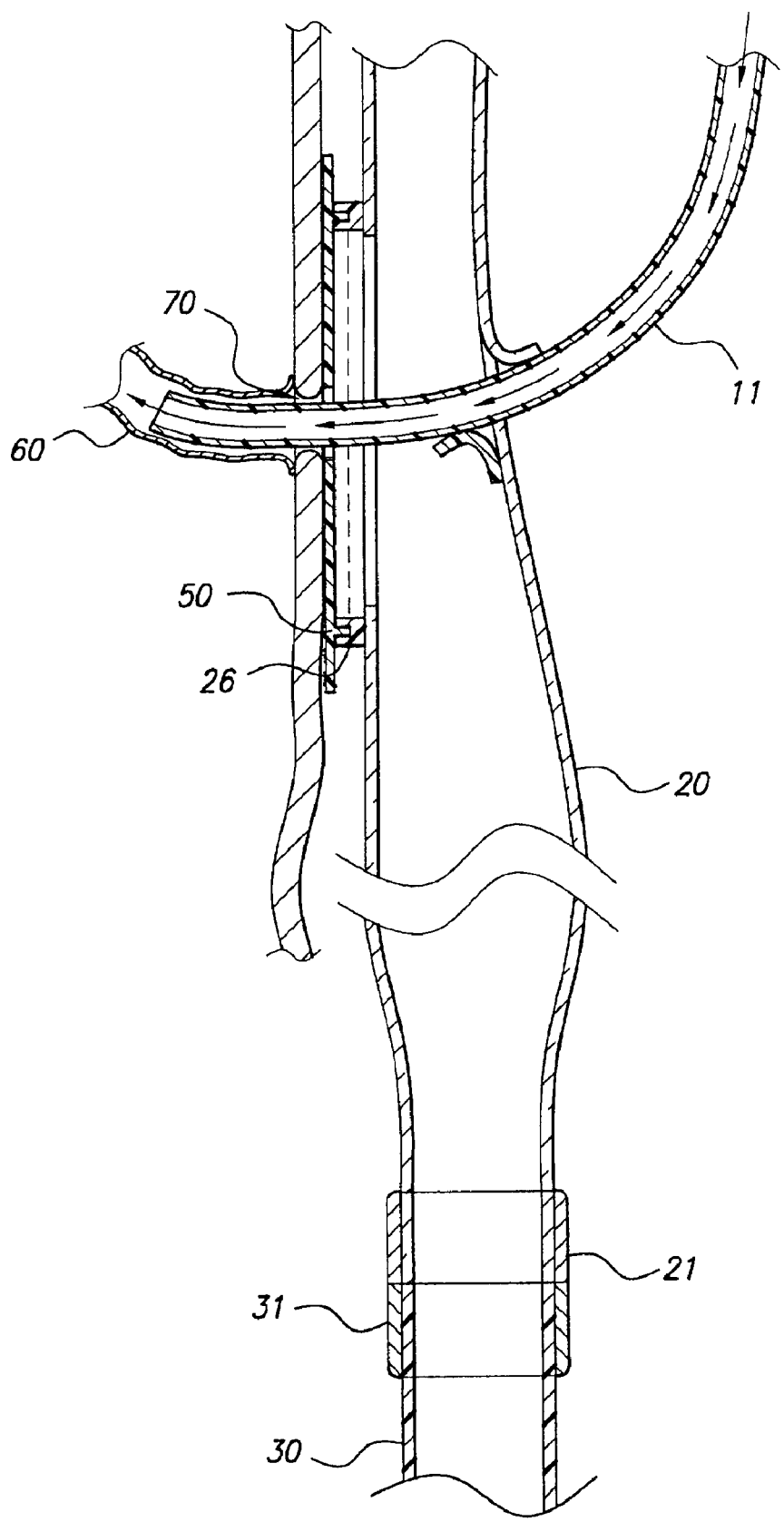
FIG. 5 is a sectional view of the colostomy bag component and enema bag tube, as used for ostomy irrigation, according to the present invention.

FIG. 5 of the drawings presents a sectional view of the colostomy bag component as used for ostomy irrigation. The enema bag tube 11 is inserted through the flapped opening 23, through the colostomy bag 20, and approximately two inches inside the user's ostomy 70. Although ostomies vary in size, typically the diameter of the tube 11 is smaller than that of the ostomy 70 and therefore the ostomy 70 does not form a perfect seal around the tube 11. As a result, the user or an assistant must hold the tube 11 in place by gripping it at a point outside of the colostomy bag 20.

The rimmed opening 25 of the colostomy bag mates with the flanged ring 50 which is secured to the user's abdomen. The rim 26 of the rimmed opening 25 and the flange 50 form an air tight seal.

As water flows out of the enema bag tube and into the colon 60, the water fills and flushes the user's colon 60. If the user's ostomy 70 is small enough to form a seal around the tube, water will be retained in the colon 60 until the tube is removed. Typically, however, the ostomy 70 does not form a seal around the tube 11 and some water flows or trickles out of the ostomy 70 during the irrigation process. Once the appropriate amount of water has flowed into the colon 60, the enema bag tube 11 is removed from the ostomy 70 and the colostomy bag 20, and the products of irrigation flow freely out of the colon 60.

After flowing out of the colon 60, the products of irrigation pass through the flanged ring 50 and the rimmed opening 25, through the colostomy bag 20, down the collection bag tube 30 and into the collection bag 40.

Figure 6:
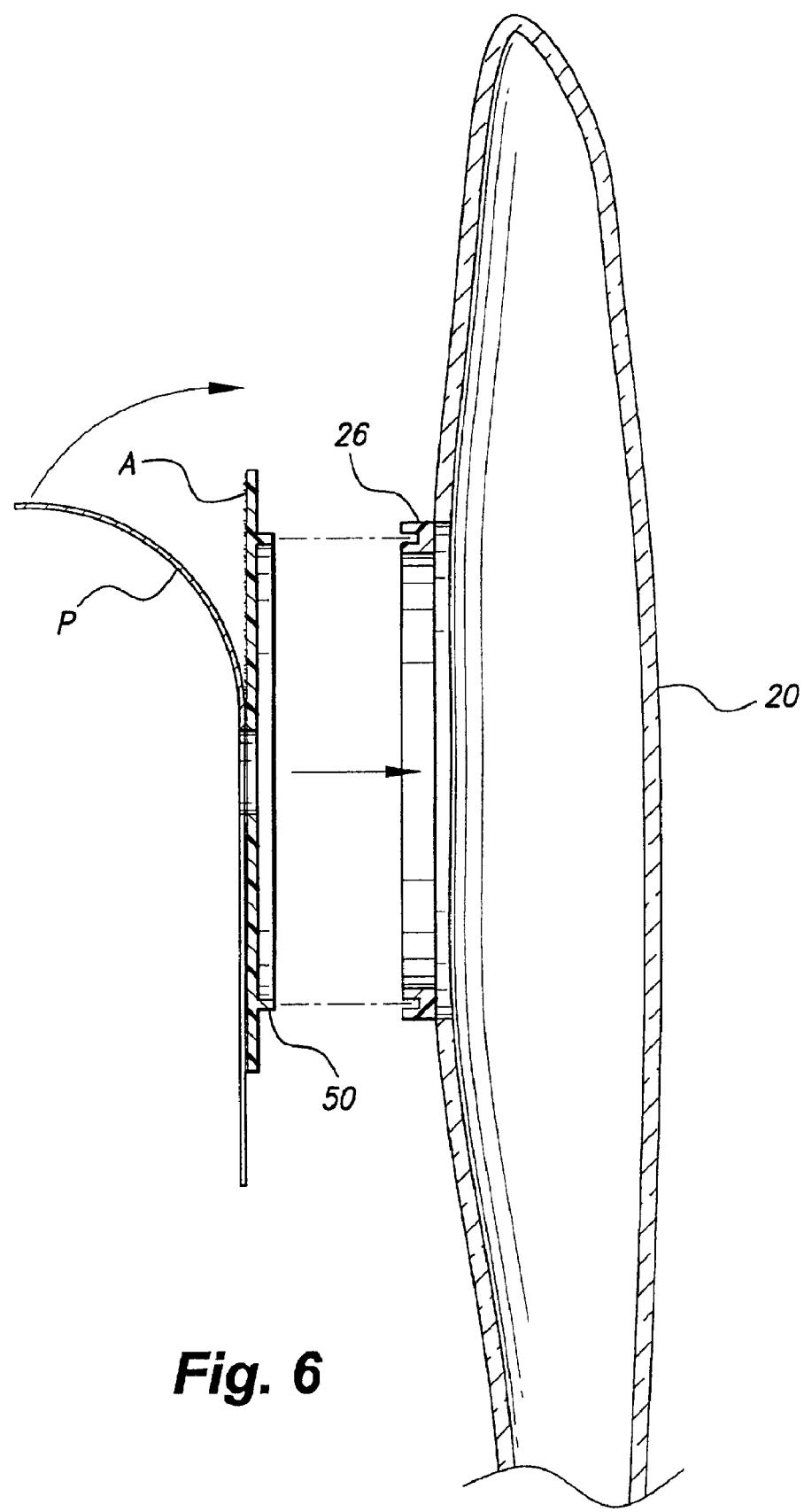
FIG. 6 is an exploded sectional view of a standard ostomy flanged ring and the rimmed opening of the colostomy bag according to the present invention.

FIG. 6 of the drawings presents a sectional view of a standard ostomy flanged ring 50 and the rim 26 about the opening 25 of the colostomy bag 20 prior to use.

The back of the flanged ring 50 is coated with an adhesive A. Prior to use, a paper covering P is peeled away from the back of the flanged ring 50 thereby exposing the adhesive A. The flanged ring 50 is then attached to the abdomen and positioned so that it surrounds the ostomy.

Prior to irrigation, the rim 26 of the rimmed opening 25 is attached to the flanged ring 50.

It is to be understood that the present invention is not limited to the embodiment described above, but encompasses any and all embodiments within the scope of the following claims.

I claim:

1. A closed drainage system for irrigating ostomies comprising:

(a) a colostomy bag having a drain opening, a stoma opening, and a supply opening defined therein;

(b) a rim attached to said colostomy bag about said stoma opening, said rim being adapted for attachment to an ostomy flange attached to a patient's ostomy and forming a watertight seal therewith;

(c) a collection bag having at least one hook attached thereto, whereby said collection bag is capable of being hung from a hospital bed;

(d) a collection bag tube connected between said drain opening and said collection bag;

(e) an enema bag; and (f) an enema bag tube having a first end attached to said enema bag and a second end adapted for insertion through the supply and stoma openings in said colostomy bag and into the patient's ostomy;

whereby an irrigation fluid may be drained from said enema bag through said enema tube into the patient's ostomy to irrigate the colon, and whereby the enema tube may be removed from the patient's ostomy in order to drain the irrigation fluid and waste products through said collection bag tube into said collection bag.

2. The closed drainage system for irrigating ostomies according to claim 1, wherein:

(a) said colostomy bag further comprises a first fitting disposed about said drain opening; and (b) said collection bag tube further comprises a first end having a second fitting mating with said first fitting to form a watertight seal, said second fitting having a stopcock valve disposed therein, whereby outflow from said colostomy bag may be temporarily interrupted during drainage of said colostomy bag.

3. The closed drainage system for irrigating ostomies according to claim 1, wherein the colostomy bag is made of a transparent material for visualizing insertion of the enema tube into a patient's ostomy.

4. The closed drainage system for irrigating ostomies according to claim 1, wherein the collection bag tube is constructed of a transparent material.

5. The closed drainage system for irrigating ostomies according to claim 1, wherein the collection bag tube is constructed of an opaque impervious material.

6. The closed drainage system for irrigating ostomies according to claim 1, wherein the collection bag is constructed of a transparent material.

7. The closed drainage system for irrigating ostomies according to claim 1, wherein the collection bag is constructed of an opaque impervious material.

8. A closed drainage system for irrigating ostomies comprising:

(a) a colostomy bag having a drain opening, a stoma opening, and a supply opening defined therein, wherein said colostomy bag further includes overlapping inner and outer flaps defining the supply opening;

(b) a rim attached to said colostomy bag about said stoma opening, said rim being adapted for attachment to an ostomy flange attached to a patient's ostomy and forming a watertight seal therewith;

(c) a collection bag;

(d) a collection bag tube connected between said drain opening and said collection bag;

(e) an enema bag; and (f) an enema bag tube having a first end attached to said enema bag and a second end adapted for insertion through the supply and stoma openings in said colostomy bag and into the patient's ostomy;

whereby an irrigation fluid may be drained from said enema bag through said enema tube into the patient's ostomy to irrigate the colon, and whereby the enema tube may be removed from the patient's ostomy in order to drain the irrigation fluid and waste products through said collection bag tube into said collection bag.

9. A closed drainage system for irrigating ostomies comprising:

(a) a colostomy bag having a drain opening, a stoma opening, and a supply opening defined therein;

(b) a rim attached to said colostomy bag about said stoma opening, said rim being adapted for attachment to an ostomy flange attached to a patient's ostomy and forming a watertight seal therewith;

(c) a collection bag having a drain spout attached thereto, the drain spout having a clamp for opening and closing the drain spout in order to permit said collection bag to be emptied;

(d) a collection bag tube connected between said drain opening and said collection bag;

(e) an enema bag; and (f) an enema bag tube having a first end attached to said enema bag and a second end adapted for insertion through the supply and stoma openings in said colostomy bag and into the patient's ostomy;

whereby an irrigation fluid may be drained from said enema bag through said enema tube into the patient's ostomy to irrigate the colon, and whereby the enema tube may be removed from the patient's ostomy in order to drain the irrigation fluid and waste products through said collection bag tube into said collection bag.

* * * * *